(12) United States Patent
Hansmann et al.

(10) Patent No.: US 10,709,862 B2
(45) Date of Patent: Jul. 14, 2020

(54) DEVICE FOR WITHDRAWING AND FOR TRANSPORTING A BREATHING GAS STREAM

(71) Applicant: Drägerwerk AG & Co. KGaA, Lübeck (DE)

(72) Inventors: Hans-Ullrich Hansmann, Barnitz (DE); Andreas Hengstenberg, Reinfeld (DE); Uwe Kühn, Wesenberg (DE); Gerd Peter, Lübeck (DE); Michael Riecke, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 626 days.

(21) Appl. No.: 15/515,788

(22) PCT Filed: Oct. 5, 2015

(86) PCT No.: PCT/EP2015/001945
§ 371 (c)(1),
(2) Date: Mar. 30, 2017

(87) PCT Pub. No.: WO2016/055147
PCT Pub. Date: Apr. 14, 2016

(65) Prior Publication Data
US 2017/0326326 A1 Nov. 16, 2017

(30) Foreign Application Priority Data

Oct. 8, 2014 (DE) .................. 10 2014 014 661

(51) Int. Cl.
*A61M 16/08* (2006.01)
*A61B 5/08* (2006.01)
(Continued)

(52) U.S. Cl.
CPC .......... *A61M 16/085* (2014.02); *A61B 5/082* (2013.01); *A61B 5/097* (2013.01);
(Continued)

(58) Field of Classification Search
CPC ...... B01D 53/22; B01D 53/268; B01D 63/06; B01D 2257/80; A61B 5/082; A61B 5/097;
(Continued)

(56) References Cited

U.S. PATENT DOCUMENTS 4,298,358 A * 11/1981 Ruschke ............ B01D 19/0031
128/205.12
4,808,201 A * 2/1989 Kertzman ............ B01D 53/268
210/490
(Continued)

FOREIGN PATENT DOCUMENTS

| CN | 102599913 A | 7/2012 |
|---|---|---|
| DE | 695 00 665 T2 | 4/1998 |

(Continued)

*Primary Examiner* — Jason M Greene
(74) *Attorney, Agent, or Firm* — McGlew and Tuttle, P.C.

(57) ABSTRACT

A device 10 withdraws a breathing gas stream (A) from a ventilation system (B) and transports the breathing gas stream (A) to a gas analysis system (G). The device 10 has a tubular configuration with an inner side (41) and with an outer side (42) and includes two tube sections (11, 11') and a drying stage (12, 14, 22) with an inner side (43, 43') and with an outer side (44, 44'), and at least one liquid storage device (13, 21). The drying stage (12, 14, 22) includes a gas-tight and moisture-permeable material that transports moisture from the inner side (43, 43') of the drying stage (12, 14, 22) through the gas-tight and moisture-permeable material to the outer side (42) of the tubular device (10). The
(Continued)

drying stage (12, 14, 22) and/or the liquid storage device (13, 21) is arranged at least partially between the two tube sections (11, 11').

20 Claims, 3 Drawing Sheets

(51) Int. Cl.
    *A61B 5/097*     (2006.01)
    *A61M 16/10*     (2006.01)
    *B01D 53/26*     (2006.01)
    *B01D 53/22*     (2006.01)

(52) U.S. Cl.
    CPC ...... *A61M 16/0808* (2013.01); *A61M 16/106* (2014.02); *A61M 16/1055* (2013.01); *B01D 53/22* (2013.01); *B01D 53/268* (2013.01); *A61M 2205/7536* (2013.01); *B01D 2257/80* (2013.01)

(58) Field of Classification Search
    CPC .............. A61M 16/085; A61M 16/106; A61M 16/0165; A61M 2205/7536
    See application file for complete search history.

(56) References Cited

U.S. PATENT DOCUMENTS

| | | |
|---|---|---|
| 6,783,573 B2 | 8/2004 | Richardson |
| 2005/0161042 A1 | 7/2005 | Fudge et al. |
| 2011/0237969 A1* | 9/2011 | Eckerbom .............. A61B 5/097 600/532 |
| 2011/0288512 A1* | 11/2011 | Locke .................. B01D 53/268 604/319 |
| 2013/0098360 A1 | 4/2013 | Hurmez et al. |
| 2014/0319706 A1* | 10/2014 | Huizing ............... B01D 53/228 261/102 |
| 2015/0151074 A1* | 6/2015 | Hermez ............ A61M 16/0875 128/203.27 |
| 2015/0238119 A1* | 8/2015 | Colman ................. A61B 5/097 600/543 |
| 2017/0184317 A1* | 6/2017 | Huizing ................. B01D 69/12 |

FOREIGN PATENT DOCUMENTS

| | | |
|---|---|---|
| DE | 10 2012 220 565 A1 | 3/2014 |
| EP | 0 535 379 A1 | 4/1993 |
| EP | 2 730 221 A1 | 5/2014 |
| WO | 2010/030226 A1 | 3/2010 |
| WO | 2011/103585 A2 | 8/2011 |
| WO | 2014/003579 A1 | 1/2014 |

\* cited by examiner

DEVICE FOR WITHDRAWING AND FOR TRANSPORTING A BREATHING GAS STREAM

CROSS REFERENCE TO RELATED APPLICATIONS

This application is a U.S. National Phase Application of International Application PCT/EP2015/001945, filed Oct. 5, 2015, and claims the benefit of priority under 35 U.S.C. § 119 of German Application 10 2014 014 661.8, filed Oct. 8, 2014, the entire contents of which are incorporated herein by reference.

FIELD OF THE INVENTION

The present invention pertains to a device which is used for withdrawing a breathing gas stream from a ventilation system and for transporting the breathing gas stream to a gas analysis system, as well as to a system with such a device.

BACKGROUND OF THE INVENTION

To monitor the breathing gas composition of a patient, for example, in case of mechanical ventilation, a breathing gas sample is usually taken at the mouthpiece or at the Y-piece of the ventilator or of the ventilation system and this is analyzed by means of gas sensors. Constituents of the breathing gas, such as $CO_2$, oxygen or also anesthetic gases, are typically monitored here continuously. It is important in case of such a continuous monitoring to protect the sensor system (i.e., the gas analysis system) from unintended moisture effects, for example, from water or condensation from the humid breathing air, as well as from biological material, e.g., bacteria, and other contaminants.

WO 2011/103585 A2 proposes in this connection a water trap, which has a filter consisting of a hydrophilic and microporous material. A breathing gas stream can be sent through the water trap. The filter can absorb water of condensation contained in the breathing gas stream and store it. WO 2011/103585 A2 provides, in addition, for an additional hydrophobic filter membrane at the outlet of this device. This filter membrane shall prevent excess liquid from being able to pass through in case of saturation of the hydrophilic filter.

WO 2010/030226 A1 provides for a sample gas line, with which a breathing gas stream can be sent from the patient to a patient gas monitor. This sample gas line is provided with a drying device. This drying device is arranged at the end of the sample gas line directly in front of the patient gas monitor. The breathing gas flowing through the sample gas line is therefore cooled to room temperature level when it reaches the drying device, and excess moisture is removed by condensation. The drying device comprises a moisture-permeable and gas-tight polyether/polyamide block copolymer housing, which is filled with a hydrophilic material.

SUMMARY OF THE INVENTION

Based on this, an object of the present invention is to provide an improved device for withdrawing and for transporting breathing gases between a ventilation system and a gas analysis device. It shall be possible by means of such an improved device, among other things, to ensure that no liquids, contaminants or microorganisms will enter the gas analysis device.

In a device for withdrawing a breathing gas stream from a ventilation system and for transporting the breathing gas stream to a gas analysis system, the present invention makes provisions for the device to have a tubular configuration with an inner side and with an outer side and to have at least two tube sections as well as at least one drying stage with an inner side and with an outer side, and at least one liquid storage device, wherein the drying stage consists at least partially of a gas-tight and moisture-permeable material such that moisture can be transported from the inner side of the drying stage through the gas-tight and moisture-permeable material to the outer side of the device, and wherein at least one drying stage and/or a liquid storage device is arranged at least partly between two tube sections.

Such a device can deliver reliable and unambiguous signals especially even when the breathing gas stream to be analyzed, which was taken from the ventilation system, has a flow rate of less than 200 mL of breathing gas per minute. In particular, it is also conceivable that such a tubular device can be used independently from the use of a conventional water trap. The device according to the present invention is therefore especially suitable for use in pediatrics and in the care of premature and newborn infants. Other possible uses are, of course, likewise not ruled out.

Another advantage of the device according to the present invention is that—independently from whether or not an additional water trap is present—liquid water drops or accumulation of water of condensation, which may possibly be contained in the breathing gas sample, can be prevented from being drawn through the gas analysis system and from damaging the gas analysis system.

The device according to the present invention may, moreover, have a very compact design, which is likewise an advantage in case the device is used in the area of pediatrics and neonatology. In addition, the development of large dead space volumes can be extensively avoided by means of this device. This is especially favorable in case of miniaturization of the breathing gas sensor system and of reduction of the sample gas flow, which is associated therewith. Another advantage is that the device according to the present invention functions in a position-independent manner. It is conceivable in this way that it can be used in mobile patient gas monitors.

A device having a tubular configuration is, for example, a tube in this connection, which has a first end and a second end. The tube may have a plurality of sections and/or subsections (tube sections, tubular section). The outer shape of the tube may be both smooth and also provided with protuberances and/or indentations having a great variety of shapes. The inner shape of the tube is preferably a duct with a round, elliptical or polygonal cross section. The inner and outer shapes may correspond to one another or be different from one another.

A tube is typically defined as a flexible line for delivering solid, liquid and/or gaseous substances. A tubular object is therefore typically an object that has the shape and function of a flexible line for delivering solid, liquid and/or gaseous substances.

The substance to be transported, for example, breathing gas, can flow through the first end into the tube and into the device. The substance being transported can again flow out of the tube or the device through the second end. The first end of the tube may therefore also be called the intake end, i.e., the end through which the breathing gas stream flows, arriving from the ventilation system, into the tubular device. The second end may be called detector end, i.e., the end through which the breathing gas stream flows out of the tubular device and is passed on to the gas analysis system. The substance can flow from the first end to the second end in the tube, i.e., consequently in the tubular device. A breathing gas flowing through the tubular device is also called breathing gas stream in the sense of the present invention.

The first end may be connected directly or indirectly to the ventilation system. For example, the first end may be connected to a tube or to an adapter, which is used to feed or remove breathing gas to and from a patient. The second end may be directly or indirectly connected to the gas analysis system.

A ventilation system may be, in connection with the present invention, any ventilator, for example, an anesthesia apparatus in the operating room or a ventilator in an intensive care unit. A gas analysis system is preferably a measuring and analysis device, which analyzes the properties of the breathing gas stream and can measure, e.g., the composition of the breathing gas stream.

A drying stage is typically a device that is installed in or attached to the tubular device, and which is used to remove water from the breathing gas stream. It is also advantageous in this connection if such a drying stage is configured to remove liquid water, for example, water drops, from the breathing gas stream.

Due to the fact that the drying stages are permeable according to the present invention to water and water vapor, but are at the same time impermeable to the other constituents of the breathing air, especially to oxygen, carbon dioxide, but also anesthetic and other constituents, separation of the moisture from the other constituents of the breathing air can be achieved.

At the same time, the slightest possible interaction between the material of the drying stages and the anesthetics possibly contained in the breathing gas is advantageous for the application in conjunction with anesthetic gases, e.g., in the suction-based patient gas measurement. It is favorable, in particular, if the anesthetics can be prevented from interacting with the material such that they will be stored in the drying stage. Therefore, modified tetrafluoroethylene polymers (PTFE), for example, sulfonated PTFE variants, e.g., Nafion® (2-[1-difluoro[(trifluoroethenyl)-oxy]methyl]-1,2,2,2-tetrafluoroethoxy]-1,1,2,2-tetrafluoroethane sulfonic acid), may preferably be used. As an alternative or in addition, it is also possible to use materials based on polyether imides or polyether block amides or polyurethane.

It is favorable in any case if the moisture can be transported directly from the inner side of the drying stage to the outer side of the device. This may be achieved, for example, by the outer side of the drying stage corresponding to the outer side of the device. The moisture can simply evaporate from there into the surrounding area and be eliminated very simply in this manner. In a preferred embodiment variant, the inner side of the drying stage corresponds, moreover, to the inner side of the device.

The drying stage is or the drying stages are preferably arranged between the intake end and the detector end. The breathing gas stream can therefore flow into the tubular device through the intake end, then flow through the at least one drying stage and finally flow out of the tubular device through the detector end.

It is conceivable in this connection that a drying stage is arranged at least partly between two tube sections. The breathing gas stream can then pass through the tubular device in the sequence of intake end, first tube section, drying stage, second tube section, and detector end. It is seen that it is favorable if the first tube section is now arranged upstream of the drying stage and the second tube section downstream of the tube section, each in relation to the flow direction of the breathing gas stream. A partial arrangement between two tube sections is defined here such that not absolutely the entire drying stage but at least a part of the drying stage is arranged between the tube sections. It is conceivable, for example, that the drying stage is arranged on the outer side of the device and a part of the drying stage protrudes into the tube between a first tube section and a second tube section, so that the breathing gas stream must flow past or through this part while flowing from the first tube section into the second tube section. This also applies in respect to the liquid storage device or liquid storage devices. An at least partial arrangement between two tube sections is conceivable and advantageous here as well.

A liquid storage device in the sense of the present invention is, for example, an element that can absorb moisture from the breathing gas stream and release it again into the breathing gas stream. For example, the liquid storage device can absorb moisture in the form of drops (liquid, water drops) from the breathing gas stream. At the same time, the liquid storage device can also release water vapor again into the breathing gas stream. It can be ensured in this way that the breathing gas stream will not become too dry due to the drying by means of the drying stage. It is also conceivable that the liquid storage device is part of the drying stage, in which case it absorbs excess moisture from the breathing gas stream like a wick. The wick is preferably arranged, as described above, between two tube sections. It is also conceivable that the device has a plurality of liquid storage devices.

A liquid storage device according to the present invention may consist, for example, of a hydrophilic, porous sintered plastic element. The sintered element may have a volume of $0.15\ cm^3$ or less. The liquid storage device may optionally consist of a nonwoven, a plasma-treated granular polyethylene (PE) material or a matrix of microstructured plastic parts. It is thus seen that it is favorable if the liquid storage device is selected from among a hydrophilic porous sintered plastic element, a nonwoven, a plasma-treated granular PE material or a matrix of microstructured plastic particles.

It is conceivable, in particular, that the liquid storage device is arranged between a first tube section and a second tube section, so that the breathing gas stream passes through the device in the sequence of
a. first tube section,
b. liquid storage device,
c. second tube section.

The liquid is removed from the breathing gas stream in this manner not only at the end of the flow section but already in the middle part or even in the front part. It is possible in this way, for example, to arrange a drying stage downstream of the liquid storage device. This drying stage may be used, for example, to lower the dew point of the breathing gas stream. This is especially advantageous if the dew point may have risen due to the release of liquid, e.g., in the form of vapor, from the liquid storage device.

It is also advantageous in this connection if at least one tube section is configured as a drying stage. The device may be configured, for example, such that the breathing gas stream passes through the device in the sequence of a) first tube section, b) liquid storage device, c) tube section configured as a drying stage. The sequence of a) tube section configured as a drying stage, b) liquid storage device, c) tube section is, of course, also conceivable as an alternative.

It is, however, especially advantageous in this connection if the liquid storage device is arranged between two tube sections configured as a drying stage. The breathing gas stream, which flows through the device, can first be dried in this manner by the first drying stage. If the breathing gas stream is especially humid or it still contains water drops, these can be absorbed by the liquid storage device. If moisture was returned from the liquid storage device into the breathing gas stream, the breathing gas stream can then be dried again by means of the second drying stage. The returning of moisture, especially in the vapor form, offers the advantage that the service life of the device can ultimately be prolonged.

It is thus seen that it is favorable if the device has a first drying stage and at least one second drying stage, and the liquid storage device is arranged between the first drying stage and the second drying stage such that the breathing gas stream passes through the device in the sequence of a. first drying stage,
b. liquid storage device, and
c. second drying stage.

It is preferred in any case if the tube sections have each a diameter that is suitable for making possible a breathing gas stream of 50 mL per minute. In case of a desired sample gas stream of 50 mL per minute, a suitable tube internal diameter is about 1 mm for a gas velocity>1 m/sec. The length of the tube sections configured as drying stages is now obtained from the necessary exchange surface, which comes into contact with the sample gas, in order to achieve the desired dehumidification and hence the necessary dew point reduction.

It is advantageous in this connection if at least one liquid storage device has a tubular configuration. It is conceivable, for example, that the device comprises in an especially simple embodiment variant a first tube section, which is configured as a drying stage; a second tube section, which is configured as a liquid storage device; and a third tube section, which is again configured as a drying stage. The intake end may be formed in the first tube section, the detector end may be formed in the third tube section, the second tube section directly adjoining the first tube section and the third tube section.

The drying effect of the drying stages can optionally be enhanced in this and in all other conceivable exemplary embodiments, whether they are described here or not, by said drying stages being provided on their outer sides with an additional desiccant. For example, zeolites with pore sizes of about 4 Å or silica gel are suitable for this. The surface or length of the drying stages can be additionally reduced in this manner, so that material can be saved as another favorable effect. It is thus seen that it is favorable if a desiccant, preferably zeolite, silica gel or the like, is applied to the outer side of at least one drying stage.

In another embodiment variant according to the present invention, the device may have a drying element, which comprises a drying stage and a liquid storage device. The liquid storage device can absorb the moisture from the breathing gas stream and send it to the drying stage. It is conceivable in this connection that the drying stage is arranged on the outer side of the device, while the liquid storage device is arranged partly between two tube sections of the device. The liquid storage device protrudes here into the drying stage. It is seen, in other words, that at least one liquid storage device is arranged in one of the drying stages, so that it forms a part of a drying element, or, in other words, it is favorable if at least one liquid storage device is a part of a drying stage.

To make it possible to effectively guide the moisture from the breathing gas stream to the drying stage by means of such a drying element, it is advantageous if at least one liquid storage device has a wick-shaped configuration. In particular, this is advantageously the liquid storage device that is arranged in the drying stage of the drying element.

It is also conceivable that a device according to the present invention has a combination of tubular drying stages, tubular liquid storage devices and/or drying elements, in which a liquid storage device as described above is arranged in a drying stage. For example, a first tube section, which is configured as a drying stage, may thus be followed by a second tube section, which is likewise configured as a drying stage, and a wick-shaped liquid storage device of a drying element is arranged between these tube sections or it protrudes into the breathing gas stream, while the drying stage that forms the drying element together with the wick-shaped liquid storage device is arranged on the outer side of the device.

It is common to all embodiments that it is advantageous if the gas-tight, moisture-permeable material of the drying stage has the slightest possible interaction with anesthetic gases possibly still contained in the breathing gas stream but the highest possible rate of permeation (water vapor permeability). It was found that it is favorable if the at least one drying stage has a membrane based on polyether imides, polyether block amides or polyurethane.

Examples of this are, e.g., the polyether block amide PEBAX™, PEBAMED™, PLATILOL™ (both from ELF Atochem Deutschland GmbH) or ARNITEL™ (from DSM). It is also conceivable that the drying stages consist of the material "V 842-1" based on polyurethane from the manufacturer Collano.

It is especially favorable in this connection if the polyurethane material is a thermoplastic material.

It is conceivable in this connection that the material of which the membrane consists is a material based on polyurethane, the membrane material having a. a density of 0.5 $g/cm^3$ to 1.8 $g/cm^3$, preferably 0.7 $g/cm^3$ to 1.5 $g/cm^3$, especially preferably 1.3 $g/cm^3$ and especially preferably 1.2 $g/cm^3$+0.1 $g/cm^3$,
b. a melting range between 100° C. and 200° C., preferably between 120° C. and 180° C., especially preferably between 140° C. and 170° C. and especially preferably between 150° C. and 160° C., and/or
c. a water vapor permeability greater than 500 $g/m^2$ per 24 hours, preferably greater than 1,000 $g/m^2$ per 24 hours, especially preferably greater than 1,500 $g/m^2$ per 24 hours, and especially preferably greater than 2,000 $g/m^2$ per 24 hours.

The gas-tight, moisture-permeable material may have, for example, a density of 1.2+0.1 $g/cm^3$, a melting range of 150° C. to 160° C. and a water vapor permeability greater than 2,000 $g/m^2$ per 24 hours. A melting range that is higher than 120° C. is especially advantageous with respect to thermal sterilization. It may also be advantageous if the membrane is applied to a polyethylene carrier. Other thermoplastic plastics are also conceivable as carriers as an alternative.

It is also conceivable in any case that the device has a hydrophobic bacteria filter, said bacteria filter preferably having a PTFE membrane with a pore size of 0.45 μm or less and a water penetration pressure of 100 kPa or higher. Such a bacteria filter may additionally prevent contamination of the gas analysis system by bacteria or other microorganisms. The bacteria filter may be used as an additional liquid barrier. It is also conceivable in this connection that the liquid storage device and the bacteria filter form a single component. This is, for example, an especially compact design.

As another aspect, the present invention provides for a system for monitoring the breathing gas of a patient, comprising the device according to the present invention. The present invention now has the features and advantages described above in detail. The use of such a system for monitoring the breathing gas of a premature or newborn infant is favorable in this connection. The use of a devoice according to the present invention for monitoring the breathing gas of a premature or newborn patient is also advantageous according to the present invention. This also applies to use in small, mobile systems, in which a position-independent function is favorable, e.g., transport systems.

Further features, details and advantages of the present invention appear from the text of the claims as well as from the following description of exemplary embodiments on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
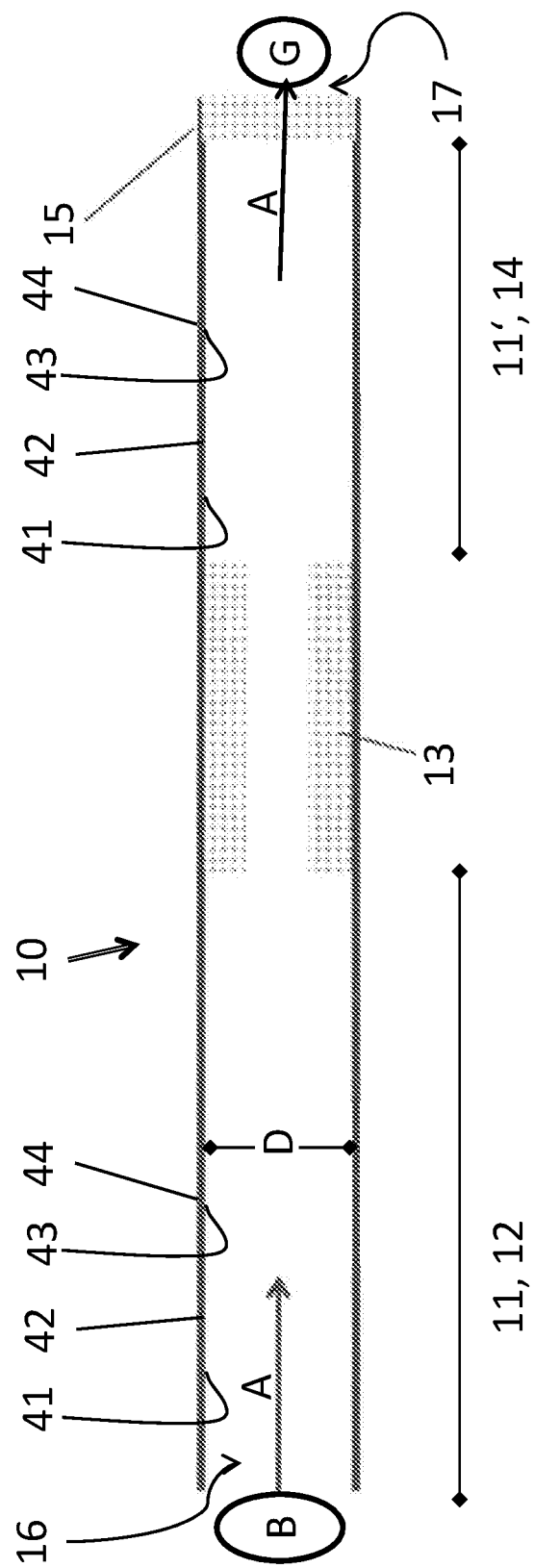
FIG. 1 is a schematic view of a first embodiment of the present invention.

Referring to the drawings, the embodiment variant of a device 10 according to the present invention shown in FIG. 1 has two tube sections 11, 11' and a liquid storage device 13 arranged between the two tube sections 11, 11'. The liquid storage device 13 has a tubular configuration corresponding to FIG. 1 in the exemplary embodiment.

Both the first tube section 11 and the second tube section 11' are configured as a drying stage 12, 14. In other words, the device 10 has a first drying stage 12 and a second drying stage 14, the drying stages 12, 14 having each a tubular configuration. The device 10 has, furthermore, an inner side 41 and an outer side 42. The drying stages 12, 14 also have an inner side 43 each and an outer side 44 each. It can be seen in this connection that the inner side 43 of the drying stages 12, 14 corresponds in the example being shown in FIG. 1 to the inner side 41 of the device 10 and that the outer side 44 of the drying stages 12, 14 corresponds to the outer side 42 of the device 10.

The drying stages 12, 14 have a gas-tight, moisture-permeable material. Suitable materials for the embodiment variant described in FIG. 1 and for all other (described or non-described) embodiment variants will hereinafter be mentioned in the example "testing of different membrane materials."

The device 10 further has a first end 16 and a second end 17. A breathing gas stream A, which arrives from a ventilation system B, can flow through the first end 16 into the device 10. The breathing gas stream A can flow out of the device 10 through the second end 17 and towards a gas analysis system G. It is seen that while flowing through the device 10, the breathing gas stream A first flows through the first drying stage 12. Moisture contained in the breathing gas stream A is transported here from the inner side 43 of the drying stage 12 and hence from the inner side 41 of the device 10 to the outer side 44 of the drying stage 12, i.e., to the outer side 42 of the device 10. If large droplets of moisture are contained in the breathing gas stream A, these can subsequently be absorbed by the liquid storage device 13. At the same time, the liquid storage device 13 may also release moisture in the form of water vapor to the breathing gas stream A. To prevent the breathing gas stream A from being greatly rehumidified in the process, moisture can once again be transported from the inner side 43 of the drying stage 14 and hence from the inner side 41 of the device 10 to the outer side 44 of the drying stage 14, i.e., to the outside 42 of the device 10 while the breathing gas stream A is passing through the second drying stage 14.

The device 10 has a diameter D. This diameter D corresponds to the internal diameter of the tube sections 11, 11'. The drying stages 12, 14 thus have the same diameter D as the entire device 10. The diameter D is selected to be such that the breathing gas stream A will have a minute volume of 50 mL/minute at a gas velocity higher than 1 m/sec. The diameter D is about 1 mm in a preferred embodiment variant.

A bacteria filter 15 is arranged as an additional protection at the second end 17 of the device 10. The bacteria filter 15 is hydrophobic and consists of a PTFE membrane with a pore size of 0.45 μm or less and with a water penetration pressure of 100 kPa or higher.

On the whole, a device 10 for withdrawing breathing gas stream A from a ventilation system B and for transporting the breathing gas stream A to a gas analysis system G is seen in FIG. 1, the device 10 having a tubular configuration with an inner side 41 and with an outer side 42 and two tube sections 11, 11' as well as two drying stages 12, 14 with an inner side 43 and an outer side 44 each, and a liquid storage device 13, the drying stages 12, 14 consisting at least partly of a gas-tight and moisture-permeable material, such that moisture can be transported from the inner side 43 of the drying stages 12, 14 through the gas-tight and moisture-permeable material to the outer side 42 of the tubular device 10, and the liquid storage device 13 being arranged between two tube sections 11.

The breathing gas stream A typically has a temperature of about 37° C. in this exemplary embodiment when it enters the first tube section 11 through the end 16. It cools while flowing through the tube section 11, as a result of which the dew point drops and water can be removed by condensation. However, this condensed water can be brought through the drying stage 12 to the outer side 42 of the device and thus removed. If water drops have formed during the cooling or have already been present in the breathing gas stream before, these are absorbed by the liquid storage device 13 during the further flow of the breathing gas stream A. However, the gas temperature can decrease further as a result and condensation of moisture may occur due to the temperature dropping below the dew point. This is likewise transported during the flow through the tube section 11', which is likewise configured as a drying stage 14, to the outer side 42 of the device 10. In addition, the condensation can be avoided by means of the drying stage 14 by the dew point of the gas being lowered by means of the drying stage 14 to below the ambient temperature. The breathing gas stream A, upon reaching the end 17, no longer has disturbing moisture present for entry into the gas analysis system G.

Figure 2:
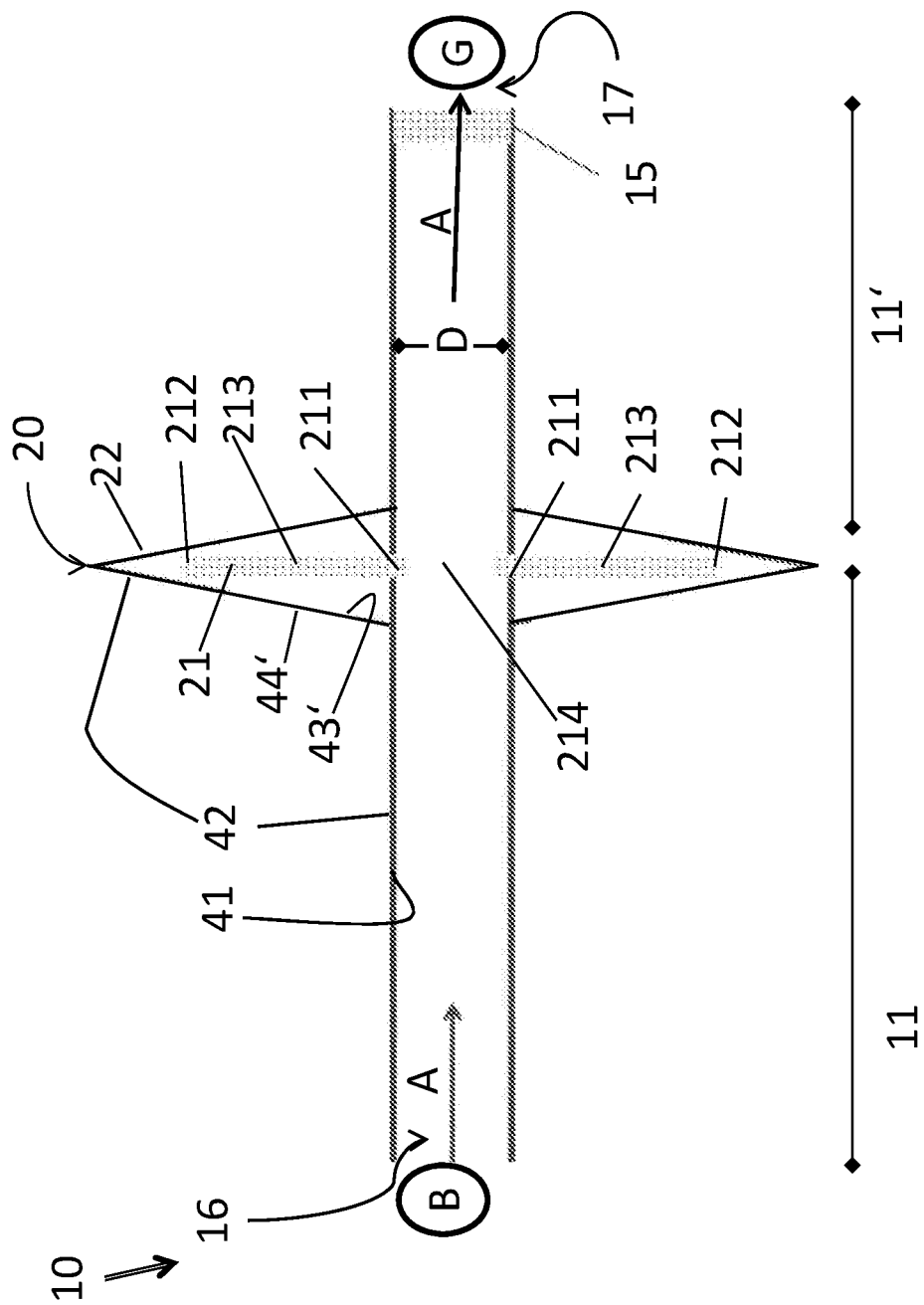
FIG. 2 is a schematic view of a second embodiment of the present invention.
Figure 3:
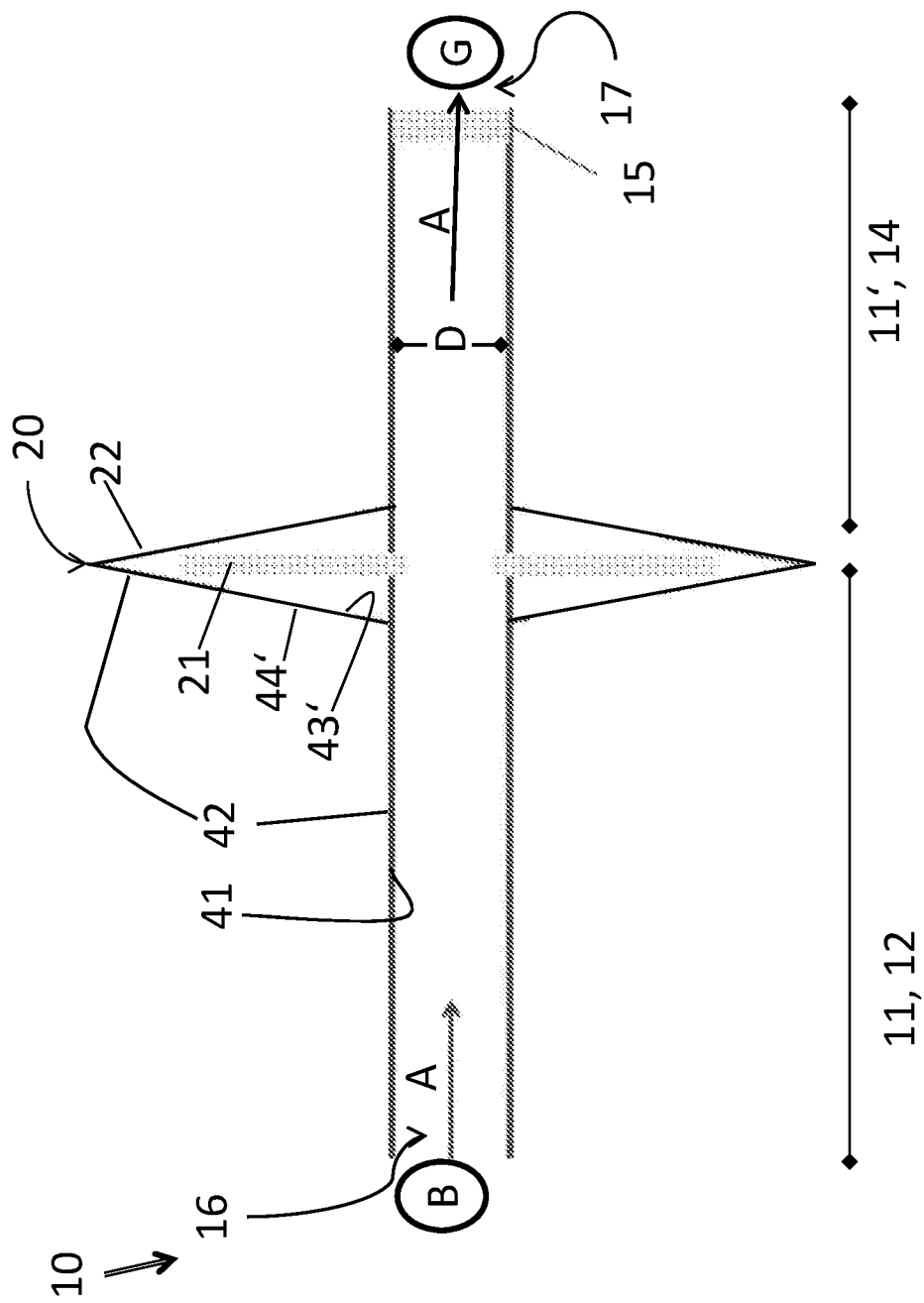
FIG. 3 is a schematic view of a third embodiment of the present invention.

The device 10 has a first tube section and a second tube section 11, 11', respectively, as well as a diameter D that is selected as was already described for FIG. 1 in the exemplary embodiments shown in FIGS. 2 and 3 as well. It is seen here as well that the device 10 has a first end 16, through which a breathing gas stream A arriving from a ventilation system B flows into the device, and a second end 17, through which the breathing gas stream A flows out of the device 10 and flows towards a gas analysis system G. The device 10 shown in FIGS. 2 and 3 also has a liquid storage device 21. This liquid storage device 21 has a wick-shaped configuration. It forms a drying element 20 together with a drying stage 22.

The wick, i.e., the liquid storage device 21, has the shape of a circular disk with a hole 214 in the center, with a circular surface 213, with an inner edge 211 and with an outer edge 212. The area of the circular surface 213 and the outer edge 212 are arranged within the drying element 22. The inner edge 211 is arranged between the first tube section 11 and the second tube section 11a. The liquid storage device 21 is thus arranged at least partly between two tube sections 11, 11'. The breathing gas stream A now flows through the hole 214. It is thus seen that at least one liquid storage device 21 is arranged in one of the drying stages 22 in the exemplary embodiment according to FIG. 2, just like in the example shown in FIG. 3, so that it forms only a part of a drying element 20. The breathing gas stream A flowing through the device 10 now flows first through the first tube section 11, then through the liquid storage device 21, namely, through the hole 214 in the liquid storage device 21, and finally through the second tube section 11'. It is thus seen that the liquid storage device 13, 21 is arranged between the first tube section and a second tube section, 11, 11', respectively, in all the exemplary embodiments shown in FIGS. 1, 2 and 3, so that the breathing gas stream A passes through the device 10 in the sequence of a. first tube section 11,
b. liquid storage device 13, 21, and
c. second tube section 11'.

The wick-shaped liquid storage device shown in FIGS. 2 and 3 may also have another shape, e.g., with a polygonal outer contour or the like, in an alternative embodiment (not shown). It is essential that it have a section that is arranged between the first and second tube sections 11, 11' and that its main surface be arranged within the drying stage 22.

The drying element 20 formed from the liquid storage device 21 and the drying stage 22 is arranged on the outer side 42 of the device 10. The outer side 44' of the drying stage 22 forms a part here of the outer side 42 of the device 10. The moisture flowing in with the breathing gas stream A is sent from the liquid storage device 21 to the inner side 43' of the drying stage 22 and reaches from the inner side 43' of the drying stage 22 the outer side 42 of the device, which corresponds in the area of the drying element 20 to the outer side 44' of the drying stage 22.

As was already described for FIG. 1, the breathing gas stream A entering the FIG. 2 typically also has a temperature of 37° C. at the first end 16. While the breathing gas stream is moving through the first tube section 11, the temperature drops here as well and water is removed by condensation. This is absorbed by the liquid storage device 21 and is sent to the drying stage 22 by means of capillary forces in order to be removed from there from the device 10 by the liquid being brought from the inner side 43' of the drying stage 22 to the outer side 42 of the device 10. After flowing through the liquid storage device 21, the cooled and dried breathing gas stream A is moved further through the second tube section 11'. The drying element 20 is ideally arranged here at the device 10 such that the breathing gas stream A is already cooled when reaching the liquid storage device 21 to the extent that no more water will be removed by condensation from the breathing gas stream A in the second tube section 11', or that the dew point of the breathing gas stream A has already decreased to the extent that no more water can be removed by condensation.

In addition to the drying element 20, the tube sections 11, 11' are configured in the exemplary embodiment shown in FIG. 3 as drying stages 12, 14, as was already explained in reference to FIG. 1. As was described for FIG. 1, these remove condensed water and/or gaseous water vapor from the breathing gas stream A to the outside to the outer side 42 of the device 10 before and after flowing through the liquid storage device 21. It is thus seen that at least one tube section 11 is configured as a drying stage 12, 14 in the exemplary embodiments shown in FIGS. 1 and 3. In particular, the device 10 has a first drying stage and at least one second drying stage 12, 14, respectively, in these embodiments, the liquid storage device 13, 21 being arranged between the first and second drying stages 12, 14 such that the breathing gas stream A passes through the device 10 in the sequence of d. first drying stage 12,
e. liquid storage device 13, 21, and
f. second drying stage 14.

The liquid storage device 13, 21 is selected from among a hydrophilic porous sintered plastic element, a nonwoven, a plasma-treated granular PE material (granular polyethylene) or a matrix of microstructured plastic particles in both the tubular liquid storage device 13 shown in FIG. 1 and the liquid storage device 21 integrated in the drying element 20 according to FIGS. 2 and 3.

It is conceivable in yet another exemplary embodiment that the device 10 has a first tube section 11 and a plurality of additional tube sections 11'. The first tube section 11 may be a simple plastic tube section, and a second tube section 11' directly adjoining same may be configured as a drying stage 12. Another tube section 11", which is configured as a liquid storage device 13 or again as a simple plastic tube, may adjoin this downstream. One or more drying elements corresponding to the drying element 20 shown in FIGS. 2 and 3 may also now be arranged downstream or also upstream. Likewise downstream, additional tube sections may follow, which are optionally configured as a drying stage, as a liquid storage device or as a simple plastic tube. It is seen here that a drying stage 12 corresponding to the present invention may also be arranged between two tube sections 11, 11'.

A desiccant, preferably zeolite, silica gel or the like, may be applied on the outer side 44, 44' of one or more drying stages 12, 14, 22 in all the embodiments shown and not shown. It is also conceivable in another, alternative exemplary embodiment, not shown, that the liquid storage device 13, 21 and the bacteria filter 15 form a single component.

The breathing gas stream A typically has a temperature of about 37° C. on entry into the device 10 through the end 16 in both the exemplary embodiment shown in FIG. 1 and in the exemplary embodiment shown in FIGS. 2 and 3 and in the exemplary embodiments that are not shown. This corresponds to the body temperature of a patient who has exhaled the breathing gas stream A. The breathing gas stream A cools due to the transport through the device 10 to the second end 17 and water can be removed by condensation from the breathing gas stream A. The dew point of the breathing gas stream A is optionally reduced here by the first drying stage 12 or 22 to the extent that it is at or below the room temperature, e.g., at about 25° C., about 20° C. or even about 15° C. Droplets may be removed by condensation in the process, and they are then taken up by the downstream liquid storage device 13 or by the hydrophobic bacteria filter 15 and stored or are sent to the drying stage 22 and released to the outside. The dew point rises again due to the removal of the droplets from the breathing gas stream A.

Testing of Different Membrane Materials

The drying stage 12, 14, 22 of the above-described exemplary embodiments consists of a gas-tight, moisture-permeable material.

Different such membrane materials were tested in Table 1 with respect to their interactions with anesthetics. A mixture of 2 vol. % of isoflurane in air was drawn alternatingly with pure air through tubes that had the corresponding membrane material, and the rise and fall times (Tup=rise time, Tdown=fall time (always T10-90 times; Trise=arithmetic mean) of anesthetics detected by a gas sensor were determined.

| Material | Thickness (μm) | g/m$^2$ | Water vapor permeability* [g/m$^2$ per 24 hours] | $T_{up}$ [msec] | $T_{down}$ [msec] | $T_{rise}$ [msec] |
|---|---|---|---|---|---|---|
| Reference without membrane | — | — | — | 424 | 460 | 442 |
| Copolyester | 15 | 21 | 1,100/2,500 | 496 | 607 | 557 |
| Polyether block amide | 15 | 10 | 1,200/2,550 | 479 | 635 | 557 |
| Polyether block amide | 22 | 25 | 1,170/2,200 | 449 | 528 | 489 |
| Polyurethane-based | 15 | 16 | 1,350/2,500 | 521 | 710 | 616 |
| Polyurethane-based | 25.4 | 32 | 720/720 | 458 | 524 | 491 |
| Polyurethane-based | 20 | 27 | 1,200/2,200 | 474 | 568 | 521 |
| Polyurethane-based | 15 | 17 | 1,200/2,200 | 433 | 496 | 465 |

*Permeation without/permeation with contact with liquid water

Materials with the properties correspondingly listed in the table are available, for example, under the following trademarks: Collano V 842-1, Epurex Platilon, API MZ 1001, Collano Tex., Arnitel VT308. The list of these materials is, of course, incomplete; other materials with corresponding properties are, of course, likewise suitable for carrying out the present invention.

It is possible in all embodiments shown that the at least one drying stage 12, 14, 22 has a membrane based on polyether imides, polyether block amides or polyurethanes. In especially preferred embodiments, the membrane consists of a material based on thermoplastic polyurethane. The membrane material has a density of 0.5 g/cm$^3$ to 1.8 g/cm$^3$, preferably 0.7 g/cm$^3$ to 1.5 g/cm$^3$, especially preferably 1 g/cm$^3$ to 1.3 g/cm$^3$ and especially preferably 1.2+0.1 g/cm$^3$; a melting range between 100° C. and 200° C., preferably between 120° C. and 180° C., especially preferably between 140° C. and 170° C. and especially preferably between 150° C. and 160° C.; and a water vapor permeability greater than 500 g/m$^2$ per 24 hours, preferably greater than 1,000 g/m$^2$ per 24 hours, especially preferably greater than 1,500 g/m$^2$ per 24 hours and especially preferably greater than 2,000 g/m$^2$ per 24 hours. For better processability, the membrane is applied to a polyethylene carrier (PE carrier).

While specific embodiments of the invention have been shown and described in detail to illustrate the application of the principles of the invention, it will be understood that the invention may be embodied otherwise without departing from such principles.

The invention claimed is:

1. A device for withdrawing a breathing gas stream from a ventilation system and for transporting the breathing gas stream to a gas analysis system, the device comprising:

an upstream tube section comprising a gas-tight and moisture-permeable material defining a gas passage for the breathing gas stream and forming an upstream drying stage with an inner side and with an outer side and configured such that moisture is transported from the inner side of the upstream drying stage through the gas-tight and moisture-permeable material of the upstream drying stage to the outer side of the upstream tube section;

a downstream tube section comprising a gas-tight and moisture-permeable material defining a gas passage for the breathing gas stream and forming a downstream drying stage with an inner side and with an outer side and configured such that moisture is transported from the inner side of the downstream drying stage through the gas-tight and moisture-permeable material of the downstream drying stage to the outer side of the downstream tube section; and at least one liquid storage device disposed downstream of the upstream drying stage and disposed upstream of the downstream drying stage and in fluid communication with the breathing gas stream for absorbing moisture from the breathing gas stream and storing absorbed moisture at the liquid storage and for releasing stored moisture from the liquid storage back into the breathing gas stream, wherein the breathing gas stream passes through the device in the sequence of the upstream drying stage of the first tube section, followed by the liquid storage device and then followed by the downstream drying stage of the second tube section, wherein the upstream tube section, the downstream tube section and the at least one liquid storage device together form a tubular configuration.

2. A device in accordance with claim 1, wherein the at least one liquid storage device is selected from among a hydrophilic porous sintered plastic material, a nonwoven, a plasma-treated granular polyethylene or a matrix of microstructured plastic particles.

3. A device in accordance with claim 1, wherein the at least one liquid storage device has a tubular configuration.

4. A device in accordance with claim 1, wherein a desiccant, comprising zeolite, silica gel or both zeolite and silica gel, is applied to the outer side of at least one drying stage.

5. A device in accordance with claim 1, further comprising a further drying stage comprising a drying element connected to the tubular configuration, wherein the at least one drying stage is arranged at least partially in the drying element.

6. A device in accordance with claim 5, wherein the at least one liquid storage device has a wick-shaped configuration.

7. A device in accordance with claim 1, wherein the at least one drying stage has a membrane based on polyether imides, polyether block amides or polyurethanes.

8. A device in accordance with claim 7, wherein the material of which the membrane is formed is a material based on polyurethane, wherein the membrane material has:
a density of 0.5 g/cm$^3$ to 1.8 g/cm$^3$; or
a melting range between 100° C. and 200° C.; or
water vapor permeability greater than 500 g/$^{M2}$ per 24 hours; or
any combination of a density of 0.5 g/cm$^3$ to 1.8 g/cm$^3$ and a melting range between 100° C. and 200° C. and a water vapor permeability greater than 500 g/$^{M2}$ per 24 hours.

9. A device in accordance with claim 7, wherein the membrane is applied to a polyethylene carrier.

10. A device in accordance with claim 1, further comprising a hydrophobic bacteria filter, wherein the bacteria filter has a PTFE membrane with a pore size of 0.45 μm or less and with a water penetration pressure of 100 kPa or higher.

11. A device in accordance with claim 10, wherein the liquid storage device and the bacteria filter form a single component.

12. A system for monitoring the breathing gas of a patient, the system comprising a device for withdrawing a breathing gas stream from a ventilation system and for transporting the breathing gas stream to a gas analysis system, the device comprising:
an upstream tube section comprising a gas-tight and moisture-permeable material defining a gas passage for the breathing gas stream and forming an upstream drying stage with an inner side and with an outer side and configured such that moisture is transported from the inner side of the upstream drying stage through the gas-tight and moisture-permeable material of the upstream drying stage to the outer side of the upstream tube section;
a downstream tube section comprising a gas-tight and moisture-permeable material defining a gas passage for the breathing gas stream and forming a downstream drying stage with an inner side and with an outer side and configured such that moisture is transported from the inner side of the downstream drying stage through the gas-tight and moisture-permeable material of the downstream drying stage to the outer side of the downstream tube section; and
at least one liquid storage device disposed downstream of the upstream tube section and disposed upstream of the downstream tube section and in fluid communication with the breathing gas stream for absorbing moisture from the breathing gas stream and storing moisture at the liquid storage and for releasing stored moisture from the liquid storage back into the breathing gas stream, wherein:
the breathing gas stream passes through the device in the sequence of the upstream drying stage of the first tube section, followed by the liquid storage device and then followed by the downstream drying stage of the second tube section; and
the upstream tube section, the downstream tube section and the at least one liquid storage device form a tubular configuration.

13. A system in accordance with claim 12, wherein the at least one liquid storage device is selected from among a hydrophilic porous sintered plastic material, a nonwoven, a plasma-treated granular polyethylene or a matrix of microstructured plastic particles.

14. A system in accordance with claim 12, further comprising a desiccant disposed outwardly of the outer side of at least one of the drying stages and adjacent to said at least one of the drying stages, wherein the desiccant comprises zeolite, silica gel or both zeolite and silica gel.

15. A system in accordance with claim 12, wherein the at least one liquid storage device has a tubular configuration.

16. A system in accordance with claim 1, further comprising a further drying stage comprising a drying element connected to the tubular configuration, wherein the at least one drying stage is arranged at least partially in the drying element, wherein the at least one liquid storage device has a wick-shaped configuration.

17. A device for withdrawing a breathing gas stream from a ventilation system and for transporting the breathing gas stream to a gas analysis system, the device comprising:
an upstream tube section comprising a gas-tight and moisture-permeable material defining a gas passage for the breathing gas stream and forming an upstream drying stage with an inner side and with an outer side and configured such that moisture is transported from the inner side of the upstream drying stage through the gas-tight and moisture-permeable material of the upstream drying stage to the outer side of the upstream tube section;
a downstream tube section comprising a gas-tight and moisture-permeable material defining a gas passage for the breathing gas stream and forming a downstream drying stage with an inner side and with an outer side and configured such that moisture is transported from the inner side of the downstream drying stage through the gas-tight and moisture-permeable material of the downstream drying stage to the outer side of the downstream tube section;
a liquid storage device disposed downstream of the upstream drying stage and disposed upstream of the downstream drying stage, the liquid storage device comprising an annular body of a hydrophilic porous sintered plastic material, a nonwoven material, a plasma-treated granular polyethylene material or a matrix of microstructured plastic particles, the annular body being in fluid communication with the breathing gas stream for absorbing moisture from the breathing gas stream and storing absorbed moisture in the annular body and for releasing stored moisture from the annular body back into the breathing gas stream, wherein:
the breathing gas stream passes through the device in the sequence of the upstream drying stage of the first tube section, followed by the liquid storage device and then followed by the downstream drying stage of the second tube section;
the upstream tube section, the downstream tube section and the at least one liquid storage device together form a tubular configuration;
at least one of the upstream drying stage and the downstream drying stage comprises a desiccant disposed outwardly of the outer side of tubular configuration and adjacent to said at least one of the drying stages, wherein the desiccant comprises zeolite, silica gel or both zeolite and silica gel.

18. A device in accordance with claim 17, wherein the at least one liquid storage device has a tubular configuration.

19. A device in accordance with claim 17, further comprising a further drying stage comprising a drying element connected to the tubular configuration, wherein the at least one drying stage is arranged at least partially in the drying element and has a wick-shaped configuration for wicking liquid or moisture from within the tubular configuration to outside of the tubular configuration.

20. A device in accordance with claim 1, wherein:
the at least one drying stage has a membrane based on polyether imides, polyether block amides or polyurethanes; and
the material of which the membrane is formed is a material based on polyurethane, wherein the membrane material has:
a density of 0.5 g/cm3 to 1.8 g/cm3; or
a melting range between 100° C. and 200° C.; or
water vapor permeability greater than 500 g/M2 per 24 hours; or
any combination of a density of 0.5 g/cm3 to 1.8 g/cm3 and a melting range between 100° C. and 200° C. and a water vapor permeability greater than 500 g/M2 per 24 hours.

* * * * *